United States Patent [19]
Lindsay

[11] Patent Number: 6,049,283
[45] Date of Patent: Apr. 11, 2000

[54] GAS DETECTING APPARATUS

[75] Inventor: John Lindsay, Dorset, United Kingdom

[73] Assignee: Zellweger Analytics Ltd., Orz, United Kingdom

[21] Appl. No.: 08/964,566

[22] Filed: Nov. 5, 1997

[30] Foreign Application Priority Data

Nov. 6, 1996 [EP] European Pat. Off. ............. 96308044

[51] Int. Cl.[7] .................................................. G08B 21/00
[52] U.S. Cl. .......................... 340/635; 340/632; 73/23.2; 73/23.21
[58] Field of Search ..................... 340/632, 628, 340/629, 630, 631, 680, 635; 73/23.2, 23.21; 324/500

[56] References Cited

U.S. PATENT DOCUMENTS

| | | | |
|---|---|---|---|
| 4,087,801 | 5/1978 | Noh | 340/680 |
| 4,506,259 | 3/1985 | Rhodes | 340/636 |
| 4,578,555 | 3/1986 | Inoue | 340/680 |
| 4,642,617 | 2/1987 | Thomas et al. | 340/680 |
| 4,707,688 | 11/1987 | Thomas | 340/680 |
| 4,831,365 | 5/1989 | Thomas et al. | 340/680 |
| 5,012,223 | 4/1991 | Griebell et al. | 340/628 |
| 5,298,889 | 3/1994 | Diei et al. | 340/680 |
| 5,331,310 | 7/1994 | Stetter et al. | 340/628 |

*Primary Examiner*—Jeffery A. Hofsass
*Assistant Examiner*—Anh La
*Attorney, Agent, or Firm*—Dilworth & Barrese

[57] ABSTRACT

The presence of a serviceable electrochemical gas sensor (1) in gas detecting apparatus is determined on the basis of the noise in the output of a sensor amplifier. A microcomputer (22) calculates mean, rms or variance values for the noise in the output of the amplifier (20) for successive periods. Each of these values is compared with the threshold and if it falls below the threshold, counter is incremented. When the counter reaches a target value, it is determined fault condition as arisen and an alarm (23) is operated.

20 Claims, 6 Drawing Sheets

GAS DETECTING APPARATUS

FIELD OF THE INVENTION

The present invention relates to a method and apparatus for detecting a fault condition in an electrochernical gas detecting apparatus.

BACKGROUND TO THE INVENTION

Electrochemical gas sensors typically comprise two or three electrodes separated by an electrolyte. These sensors generate currents in response to the presence of a gas, e.g. carbon monoxide, hydrogen sulphide, sulphur dioxide or ammonia for which they are adapted. Hitherto, faults in such sensors, for example broken signal wires or loss of electrolyte, have been detected by applying a quantity of the gas to be detected to a sensor while monitoring the sensor output. If a wire is broken or the electrolyte has leaked away, there will be no, or at least a greatly reduced, output current.

The need to test such sensors by applying quantities of gas has a number of disadvantages. Staff are required to visit each sensor which is time consuming and undesirable if a sensor is located in a clean environment such as is found in semiconductor processing plants. Also, if a sensor fails, its failure will not be detected until the next test. This of course is undesirable where the sensor is used to detect a toxic gas or an explosive gas. Furthermore, if the gas to be detected is toxic, it is undesirable that it be deliberately released during the testing process and, for domestic use in particular, this method of testing is quite unsuitable.

SUMMARY OF THE INVENTION

It is an aim of the present invention to overcome the aforementioned problems.

The present inventor has determined that fault conditions in electrochemical sensors can be detected by monitoring the noise in the sensor output. A surprising feature of electrochemical gas sensors is that the noise level decreases in the event of common fault conditions.

According to the present invention, there is provided a method of detecting a fault condition in an electrochemical gas detecting apparatus comprising the steps of: monitoring the output signal of an electrochemical gas sensor circuit; and selectively signalling an alarm condition on the basis of noise in said output signal.

According to the present invention, there is also provided a gas detecting apparatus including a circuit for producing a gas concentration dependent signal from the output of an electrochemical gas sensor, the apparatus comprising processing means for monitoring the output signal of the circuit and selectively signalling an alarm condition on the basis of noise in said output signal.

An alarm condition may be signalled if the mean noise amplitude, for a predetermined sample period, falls below a threshold. Preferably, an alarm condition is signalled if the mean noise amplitudes, for a plurality of predetermined sample periods, fall below the threshold.

An alarm condition may be signalled if the rms noise amplitude, for a predetermined sample period, falls below a threshold. Preferably, an alarm condition is signalled if the rms noise amplitudes, for a plurality of predetermined sample periods, fall below the threshold.

An alarm condition may be signalled if the noise amplitude variance, for a predetermined sample period, falls below a threshold. Preferably, an alarm condition is signalled if the noise amplitude variances, for a plurality of predetermined sample periods, fall below the threshold.

An alarm condition may be signalled if the noise amplitude or noise amplitude variance has a downward trend over a predetermined period. A downward trend in amplitude will be reflected in a downward trend in the mean or rms amplitude values. The mean noise amplitude, rrns noise amplitude or noise amplitude variance may be measured for noise falling within a predetermined bandwidth.

Advantageously, the alarm condition is signalled to a central station.

DESCRIPTION OF PREFERRED EMBODIMENTS

Embodiments of the present invention will now be described, by way of example, with reference to the accompanying drawings.

Figure 1:
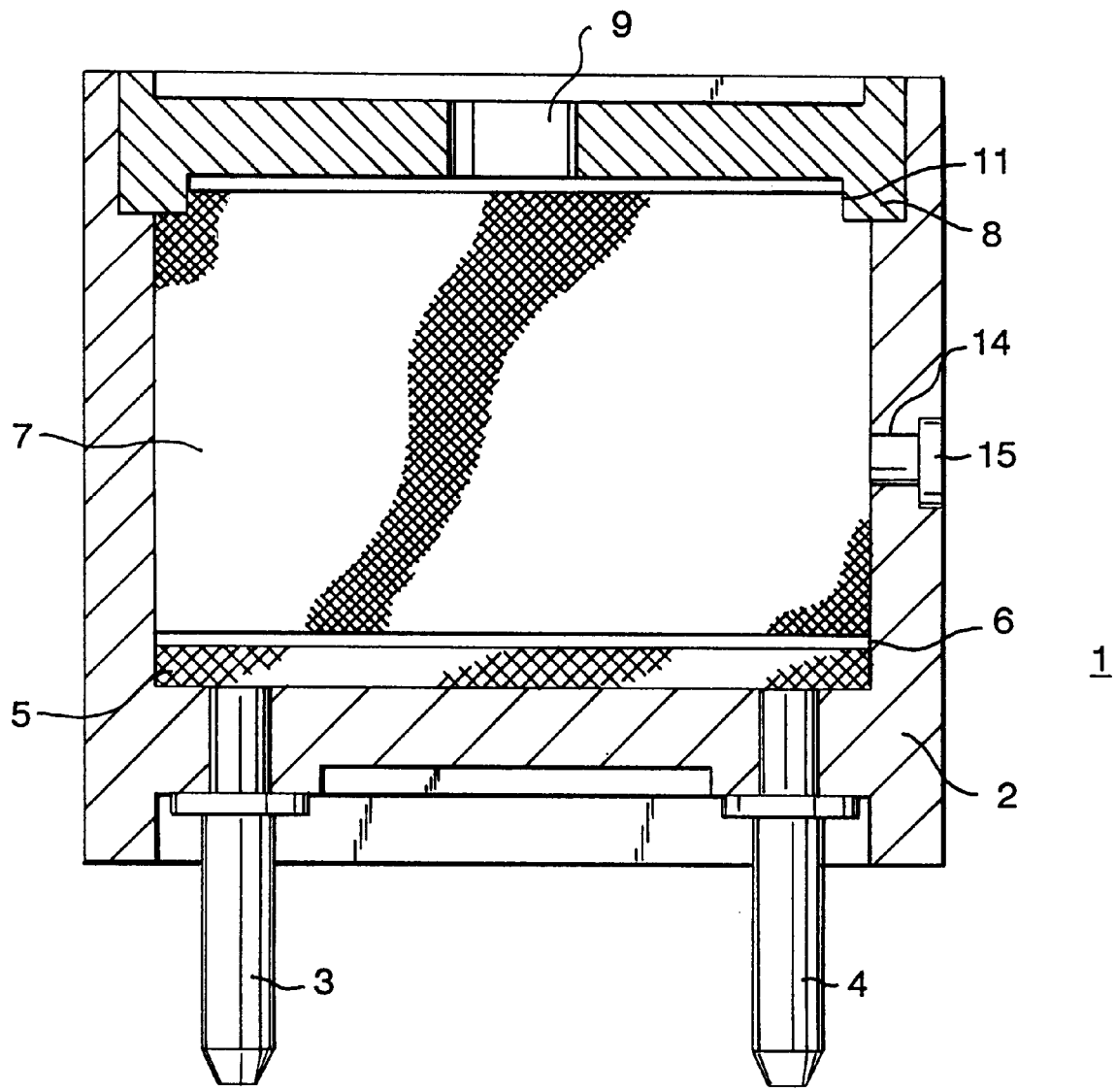
FIG. 1 is a sectional view of an electrochemical gas sensor.

Referring to FIG. 1, an electrochemical sensor 1 comprises a generally cylindrical cup 2 formed from plastics resin material. First and second contact pins 3, 4 extend through the base of the cup 2. A layer 5 of potting compound is located immediately over the floor of the cup 2. A first electrode structure 6 overlays the potting compound. A wad 7, comprising a roll of glass fibre textile, sits on top of the first electrode structure 6. The wad 7 is soaked in an electrolyte. A disc-shaped cap 8 is dimensioned to plug the open end of the cup 2. The cap 8 has an axial, centrally located hole 9 to allow gas to be sensed to pass into the cup 2. A first wire (not shown) extends from the first contact pin 3 and overlays the first electrode structure 6. A second wire (not show) extends from the second contact pin 4, up the inside of the cup 2, and between the wad 7 and the second electrode structure 11 to provide a connection thereto.

An aperture 14 is provided in the side wall of the cup 2. This aperture 14 is stopped with a plug 15.

The first electrode 6 comprises a disc of gas-permeable PTFE, coated on one face with platinum black. The coated face forms an electrode and, in the assembled sensor 1, contacts the wad 7. The second electrode structure 11 has the same construction and its coated face is also in contact with the wad 7 in the assembled sensor 1.

The first electrode 6 allows the passage of gas. However, it prevents the electrolyte escaping through the hole 9 in the cap 8. The wad 7 acts as a wick to ensure that, whatever the orientation of the sensor, the electrode structures 6, 11 remain in contact with the electrolyte.

Figure 2:
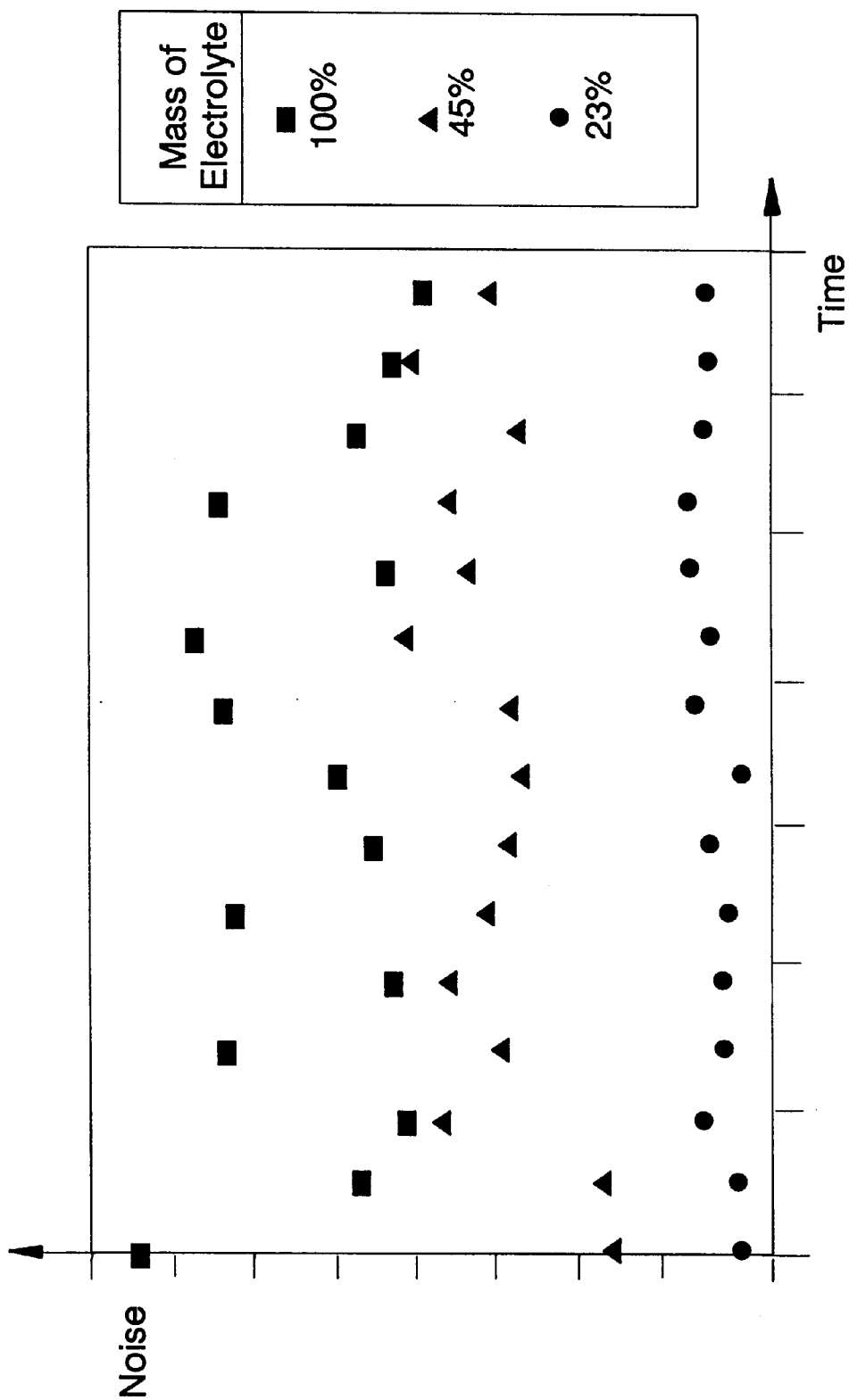
FIG. 2 is a plot of noise amplitude against time for different amounts of electrolyte in a sensor.

Referring to FIG. 2, it can be seen that the variation in noise amplitude reduces as the amount of electrolyte reduces. In the limit, i.e. no electrolyte, or if a wire in the sensor breaks, the noise comprises electromagnetic interference (EMI) and noise generated in the electronic devices used to process the sensor's output signal.

It can also be seen that, for a given amount of electrolyte, the noise amplitude values fall within a particular band. For instance, there is very little overlap between the noise amplitude values obtained with respectively 100%, 45% and 23% of the design electrolyte volume.

Figure 3:
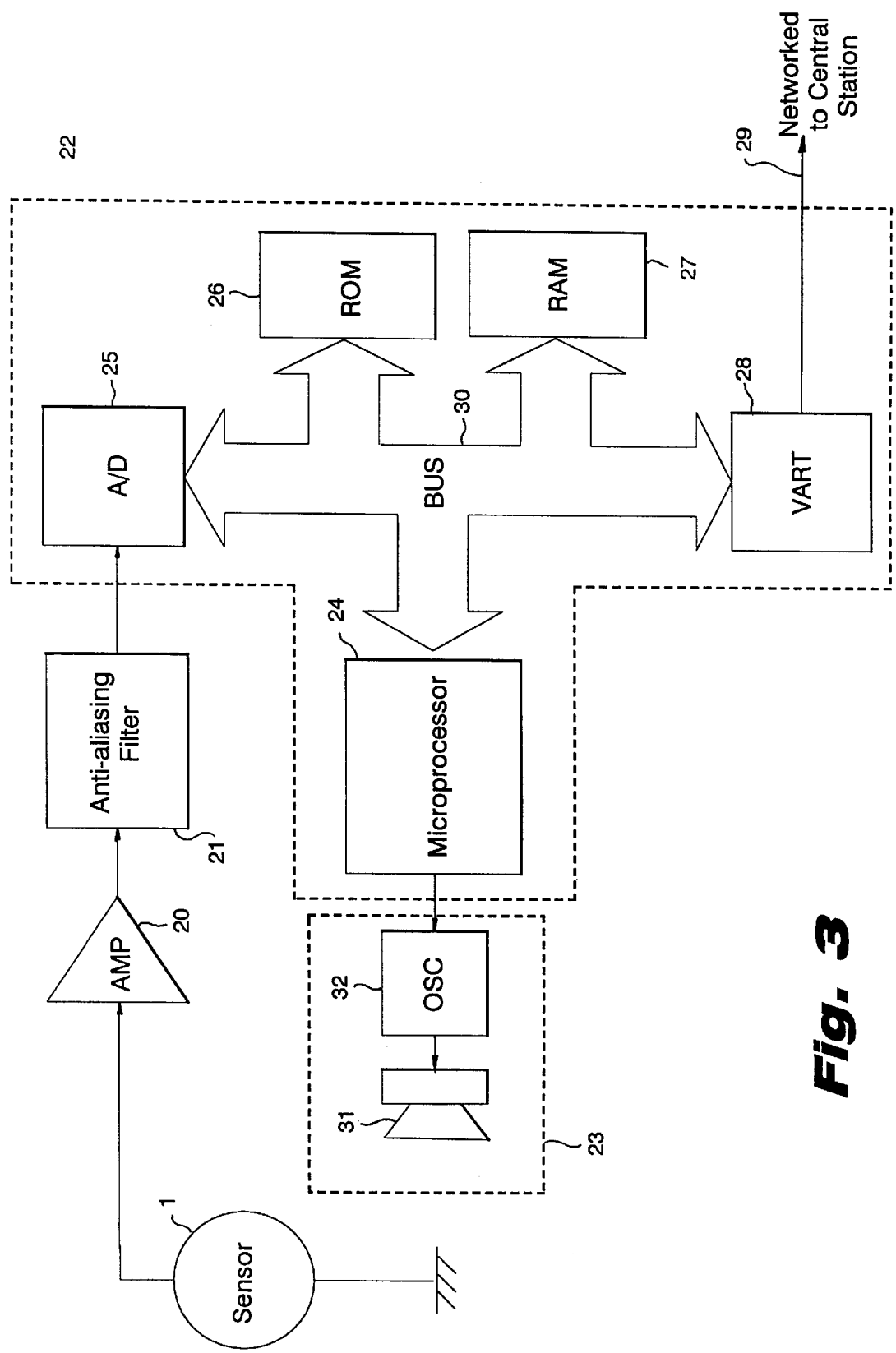
FIG. 3 is a block diagram of a gas sensing instrument.

Referring to FIG. 3, a gas sensing instrument comprises an electrochemical gas sensor 1, a current amplifier 20 for amplifying the sensor's output, an anti-aliasing filter 21 for filtering the amplifier's output, a microcomputer 22 for processing the filter's output and an alarm 23. The microcomputer 22 comprises a microprocessor 24, an analogue-to digital converter (ADC) 25 for receiving and digitizing the filter's output, a read-only memory (ROM) 26 storing a control program and constant data, a random-access memory (RAM) 27 for storing data, a universal asynchronous receiver transmitter (UART) 28 coupled to a point-to-point or network connection 29 to a central control station, and a data and address bus 30 linking the microprocessor 24, the ADC 25, the ROM 26, the RAM 27 and the UART 28. The alarm circuit 23 comprises an audio frequency oscillator 32 and a loudspeaker 31. The oscillator 32 is connected to a port of the microprocessor 24 so that it can be triggered by the microprocessor 24.

Figure 4:
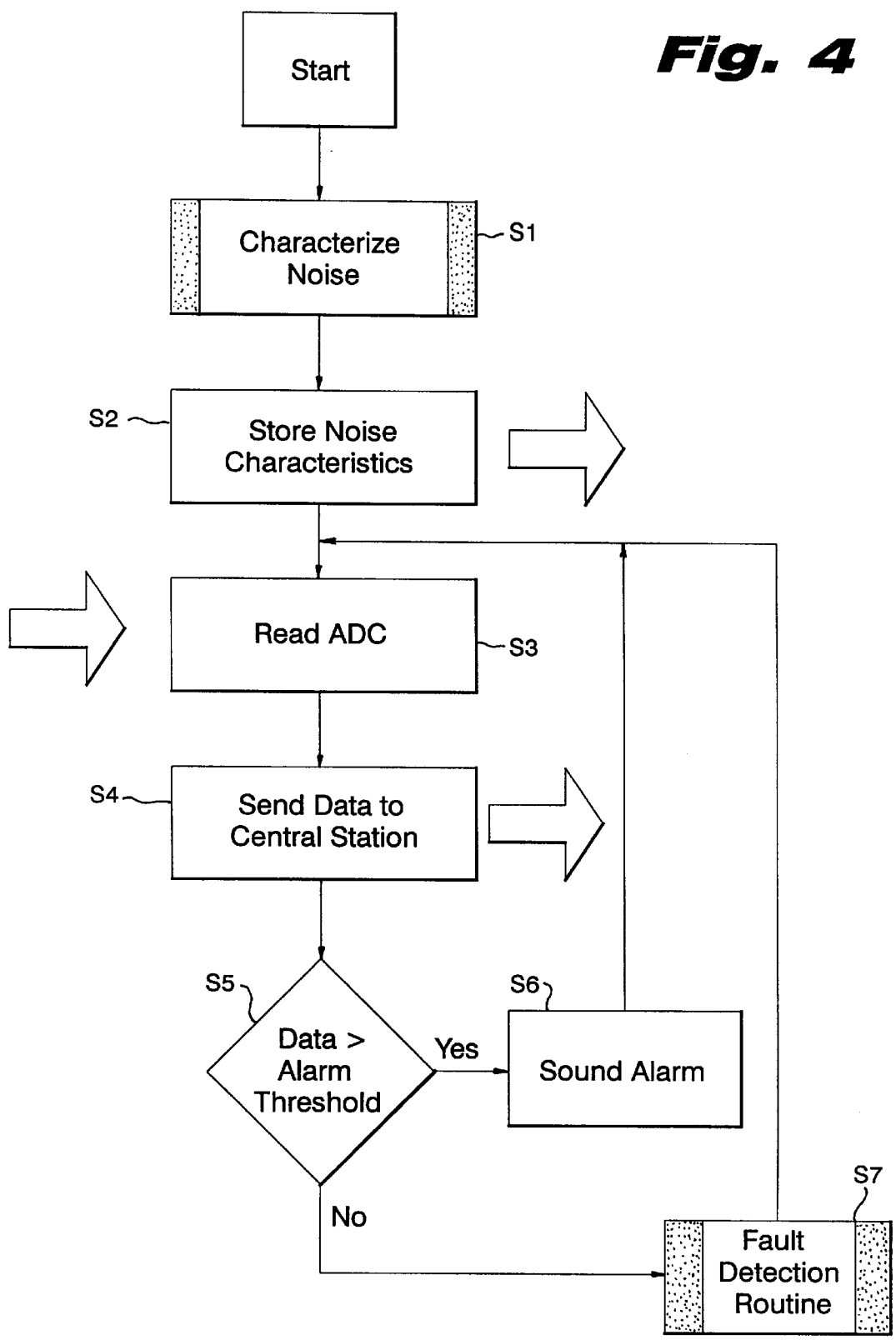
FIG. 4 is a flow chart illustrating the operation of the instrument of FIG. 3.

Referring to FIG. 4, when a new sensor 1 is inserted in the instrument and the instrument is switched on, the microprocessor 24 first performs a noise Characterize routine (step s1). This necessary because there is a significant degree of variation in noise characteristics between sensors. Once the noise has been Characterized, the microprocessor 24 stores the noise characterising data in the RAM 27 (step s2). After the noise Characterizing data has been stored, the microprocessor 24 starts performing the steps of a gas monitoring loop.

The current signal from the sensor 1 is amplified and output as a voltage signal by the amplifier 20. The anti-aliasing filter 21 then removes high-frequency components from the amplifier's output. The microprocessor 24 requests data from the ADC 25 (step s3) which responds by placing a digital representation of the current value of the filter's output on the bus 30. The microprocessor 24 sends the data from the ADC 25, together with an instrument ID code, to the UART 28 for transmission to the central control station (step s4). The microcomputer 24 then compares the data from the ADC 25 with a threshold value stored in the ROM 26 (step s5), i.e. has an unacceptable gas concentration been detected? If the data is above the threshold, the microprocessor 24 outputs an enable signal to the oscillator 32 (step s6). The oscillator 32 starts operating and drives the loudspeaker 31 to provide a local alarm. Since the failure modes of the sensor 1 mimick the no gas present condition, there is no need to perform fault detection when an alarm condition is decreased.

If, on the other hand, the data is below the threshold, the microprocessor 24 performs a fault detection routine (step s7).

First Embodiment

In a first embodiment, fault detection is based upon the mean value of the amplitude of the noise in the sensor amplifier signal. It can be seen from FIG. 2 that the mean value of the noise amplitude decreases with decreasing amount of electrolyte.

During the noise Characterization routine (step s1), the microprocessor 24 first waits for the sensor to settle, this can be a matter of minutes or several hours, and then repeatedly reads data from the ADC 25. The microprocessor 24 reads the data from the ADC 25 for a period ranging from a few seconds to a few tens of minutes, depending on the sensor used. Once all the data has been read, the microprocessor 24 calculates the mean of the magnitude of the amplitude of the noise for the ADC reading period. The microprocessor 24 then calculates a threshold value as a fraction or percentage of the calculated mean. This relationship will depend on the nature of the sensor used and the application in which the apparatus is used but may be, for instance, 60%.

Figure 5:
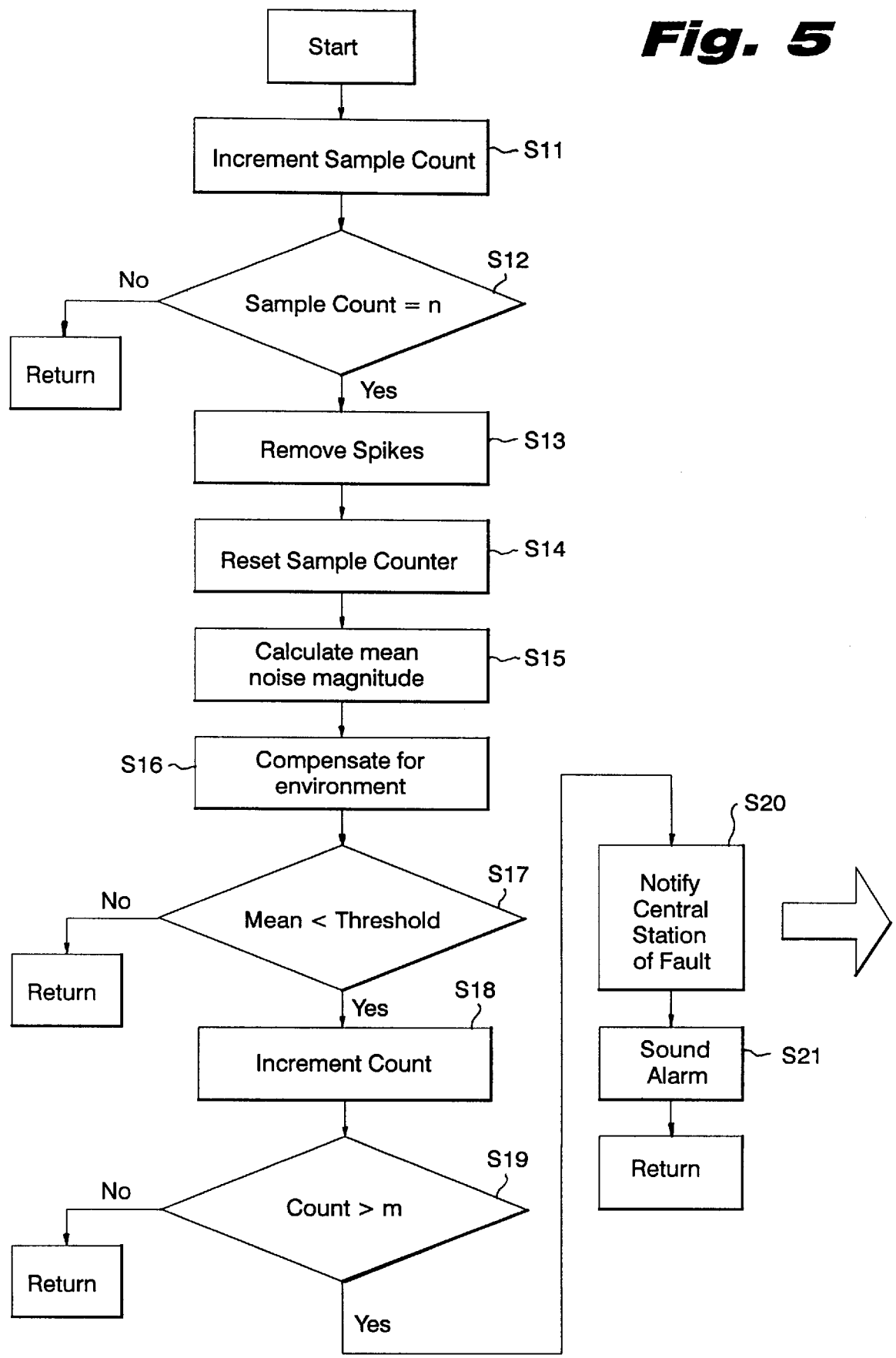
FIG. 5 is a flow chart of the fault detection routine of a first embodiment.

Referring to FIG. 5, when the microprocessor 24 enters the fault detection routine, it first increments a sample count (step s11). If the sample count does not equal a predetermined number, e.g. 255, the microprocessor 24 returns from the fault detection routine (step s12).

However, if the sample count equals the predetermined number, the microprocessor 24 processes the collected samples to remove anomalous values, e.g. spikes caused by switch operations or the like, at step s13. The sample count is then reset to zero (step s14). Once spikes and other anomalous values have been removed from the samples, the microprocessor 24 calculates the mean value of the noise for the samples (step s15). This result is compensated for environmental factors such as temperature (step s16).

The calculated mean is compared with the threshold set during the noise characterisation step s1 (step s17). If the mean is greater than the threshold, the routine is exited.

If on the other hand, the mean is below the threshold, the microprocessor 24 increments a count value (step s18). If the count is below a target level, e.g. 5, the routine is exited. If the count has reached the target level, the microprocessor 24 determines that the sensor is faulty or absent and notifies the central station (step s20). The alarm circuit 23 is then activated to sound the alarm locally (step s21).

After the alarm has sounded, the routine is exited so that gas detection can continue using whatever capability remains.

Second Embodiment

A second embodiment is similar to the first embodiment except that the rms value of the noise is used rather than the mean of the noise magnitude.

Third Embodiment

It can be seen from FIG. 2 that the range of values taken by noise reduces as the electrolyte is lost. In statistical terms, the variance of the data reduces with decreasing amount of electrolyte.

During the noise Characterization routine (step s1), the microprocessor 24 first waits for the sensor to settle, this can be a matter of minutes or several hours, and then repeatedly reads data from the ADC 25. The microprocessor 24 reads the data from the ADC 25 for a period ranging from a few seconds to a few tens of minutes, depending on the sensor used. Once all the data has been read, the microprocessor 24 calculates the variance of the noise amplitude for the ADC reading period. The microprocessor 24 then calculates a threshold value as a fraction or percentage of the calculated variance. This relationship will depend on the nature of the sensor used and the application in which the apparatus is used but may be, for instance, 60%.

Figure 6:
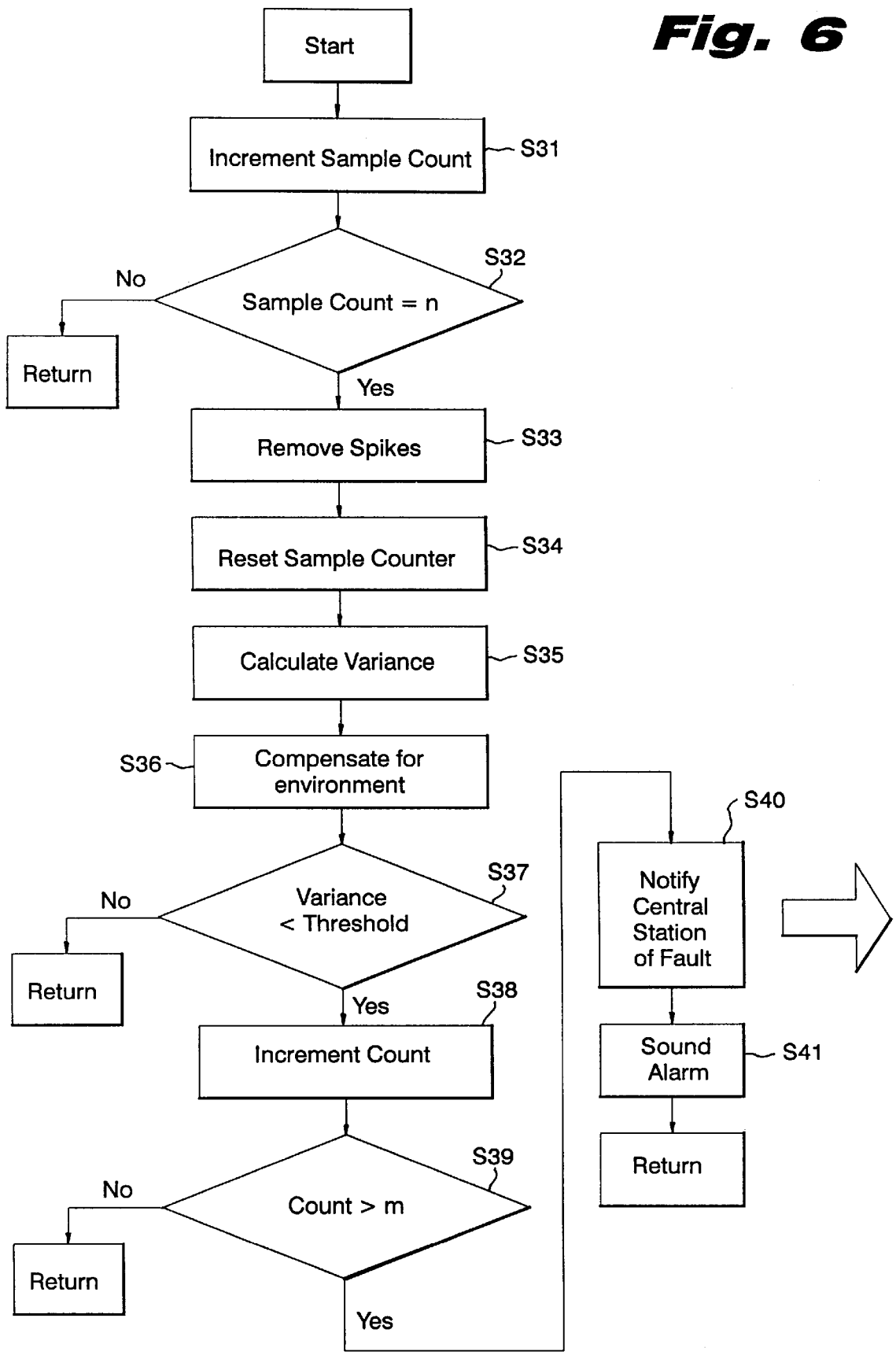
FIG. 6 is a flow chart of the fault detection routine of a third embodiment.

Referring to FIG. 6, when the microprocessor 24 enters the fault detection routine, it first increments a sample count (step s31). If the sample count does not equal a predetermined number, e.g. 255, the microprocessor 24 returns from the fault detection routine (step s32).

However, if the sample count equals the predetermined number, the microprocessor 24 processes the collected samples to remove anomalous values, e.g. spikes caused by switch operations or the like, at step s33. The sample count is then reset to zero (step s34). Once spikes and other anomalous values have been removed from the samples, the microprocessor 24 calculates the variance of the noise amplitude for the samples (step s35). This result is compensated for environmental factors such as temperature (step s36).

The calculated variance is compared with the threshold set during the noise Characterization step s1 (step s37). If the variance is greater than the threshold, the routine is exited.

If on the other hand, the variance is below the threshold, the microprocessor 24 increments a count value (step s38). If the count is below a target level, e.g. 5, the routine is exited. If the count has reached the target level, the microprocessor 24 determines that the sensor is faulty or absent and notifies the central station (step s40). The alarm circuit 23 is then activated to sound the alarm locally (step s41).

After the alarm has sounded, the routine is exited so that gas detection can continue using whatever capability remains.

Modifications

Since the noise generated in the sensor is stochastic, an average or variance value falling below the relevant threshold is not conclusive of declining electrolyte quantity; hence the need in the foregoing embodiments for the threshold to be crossed a target number of times. An alternative approach is to monitor the trend of the average or variance values over a period. If the trend is downwards during the predetermined period, it can be assumed that the amount of electrolyte in the sensor is decreasing and that an alarm should be signalled.

The performance of the first to third embodiments, described above, could be enhanced if noise energy is predominately in one or more restricted frequency bands. One or more band-pass filters, for selecting the restricted band or bands, may be placed between the sensor and the anti-aliasing filter or implemented in the microcomputer.

It will be appreciated that these and many other modifications may be made to the above described embodiments without departing from the spirit or scope of the appended claims. Any parameter of sensor circuit noise signal which varies with electrolyte quantity may be used as a basis for determining the fault condition.

What is claimed is:

1. A method of detecting a fault condition in an electrochemical gas detecting apparatus, comprising the steps of:
   setting a threshold value of an electrical noise level in an output signal of an electrochemical gas sensor circuit;
   monitoring the output signal; and
   selectively signalling an alarm condition when an electrical noise level in said output signal falls below the preset threshold value.

2. A method according to claim 1, wherein an alarm condition is signalled if a mean noise amplitude of the electrical noise level for a predetermined sample period, falls below the threshold.

3. A method according to claim 2, wherein an alarm condition is signalled if the mean noise amplitudes, for a plurality of predetermined sample periods, fall below the threshold.

4. A method according to claim 1, wherein an alarm condition is signalled if an rms noise amplitude of the electrical noise level, for a predetermined sample period, falls below the threshold.

5. A method according to claim 4, wherein an alarm condition is signalled if the rms noise amplitudes, for a plurality of predetermined sample periods, falls below the threshold.

6. A method according to claim 1, wherein an alarm condition is signalled if noise amplitude variance of the electrical noise level, for a predetermined sample period, falls below the threshold.

7. A method according to claim 6, wherein an alarm condition is signalled if the noise amplitude variance, for a plurality of predetermined sample periods, falls below the threshold.

8. A method according to claim 1, wherein an alarm condition is signalled if the electrical noise level has a downward trend over a predetermined period.

9. A method according to claim 1, wherein an alarm condition is signalled when electrical noise in the sensor circuit output signal falls within a restricted frequency band.

10. A method according to claim 1, wherein the alarm condition is signalled to a central station.

11. A gas detecting apparatus including a circuit for producing a gas concentration dependent signal from an output of an electrochemical gas sensor, the apparatus comprising processing means for monitoring the output signal of the circuit and selectively signalling an alarm condition when an electrical noise level in said output signal falls below a predetermined threshold value.

12. An apparatus according to claim 11, wherein the processing means is operative to signal an alarm condition if a mean noise amplitude of the electrical noise level, for a predetermined sample period, falls below the threshold.

13. An apparatus according to claim 12, wherein the processing means is operative to signal an alarm condition if the mean noise amplitudes, for a plurality of predetermined sample periods, fall below the threshold.

14. An apparatus according to claim 11, wherein the processing means is operative to signal an alarm condition if an rms noise amplitude of the electrical noise level, for a predetermined sample period, falls below the threshold.

15. An apparatus according to claim 14, wherein the processing means is operative to signal an alarm condition if the rms noise amplitudes, for a plurality of predetermined sample periods, fall below the threshold.

16. An apparatus according to claim 11, wherein the processing means is operative to signal an alarm condition if a noise amplitude variance of the electrical noise level, for a predetermined sample period, falls below the threshold.

17. An apparatus according to claim 16, wherein the processing means is operative to signal an alarm condition if the noise amplitude variances, for a plurality of predetermined sample periods, fall below the threshold.

18. An apparatus according to claim 11, wherein the processing means is operative to signal an alarm condition if the electrical noise level has a downward trend over a predetermined period.

19. An apparatus according to claim 11, including filter means for selecting electrical noise in the output signal falling within a predetermined band frequency for the determination of a fault condition.

20. An apparatus according to claim 11, including a central station and a data transmission system linking the processing means and the central station, wherein the processing mean is operative to signal the alarm condition to a central station via said data transmission system.

* * * * *